US010973603B2

(12) United States Patent
Palushi et al.

(10) Patent No.: US 10,973,603 B2
(45) Date of Patent: Apr. 13, 2021

(54) DILATION SYSTEM WITH ILLUMINATING ORIENTATION INDICATOR FEATURES

(71) Applicant: Acclarent, Inc., Irvine, CA (US)

(72) Inventors: Jetmir Palushi, Irvine, CA (US); Fatemeh Akbarian, Rancho Palos Verdes, CA (US); Thomas D. Pierson, Minneapolis, MN (US)

(73) Assignee: Acclarent, Inc., Irvine, CA (US)

( * ) Notice: Subject to any disclaimer, the term of this patent is extended or adjusted under 35 U.S.C. 154(b) by 83 days.

(21) Appl. No.: 16/052,811

(22) Filed: Aug. 2, 2018

(65) Prior Publication Data

US 2019/0076211 A1 Mar. 14, 2019

Related U.S. Application Data

(60) Provisional application No. 62/555,719, filed on Sep. 8, 2017.

(51) Int. Cl.
*A61M 29/02* (2006.01)
*A61B 1/00* (2006.01)
(Continued)

(52) U.S. Cl.
CPC .............. *A61B 90/08* (2016.02); *A61B 1/00* (2013.01); *A61M 25/0097* (2013.01); *A61M 25/0105* (2013.01); *A61M 25/04* (2013.01); *A61M 29/00* (2013.01); *A61M 29/02* (2013.01); *A61B 17/24* (2013.01); *A61B 34/20* (2016.02); *A61B 90/30* (2016.02); *A61B 2017/00455* (2013.01); *A61B 2017/00946* (2013.01);
(Continued)

(58) Field of Classification Search
CPC ............... A61B 1/00–32; A61B 90/08; A61M 29/00–02
See application file for complete search history.

(56) References Cited

U.S. PATENT DOCUMENTS 4,582,067 A * 4/1986 Silverstein ............. A61B 1/015
600/455
5,556,417 A * 9/1996 Sher .................... A61B 17/0231
600/236
(Continued)

OTHER PUBLICATIONS

U.S. Appl. No. 62/453,220, entitled "Navigation Guidewire with Interlocked Coils," filed Feb. 1, 2017.
(Continued)

*Primary Examiner* — Nicholas J Plionis
(74) *Attorney, Agent, or Firm* — Frost Brown Todd LLC (57) ABSTRACT

An apparatus includes a body and a dilation catheter operatively coupled with the body and configured to translate between proximal and distal positions. The dilation catheter includes a dilation member configured to dilate an anatomical passageway when the dilation catheter is in the distal position. A guide catheter is coupled to the body and defines a longitudinal axis. The guide catheter is selectively positionable in a plurality of rotational orientations about the longitudinal axis relative to the body, and is configured to guide the dilation catheter therethrough between the proximal and distal positions. The apparatus further includes at least one illuminating indicator feature configured to emit light to facilitate positioning of the guide catheter in one or more of the rotational orientations.

19 Claims, 8 Drawing Sheets

(51) Int. Cl.
  *A61B 90/00* (2016.01)
  *A61M 29/00* (2006.01)
  *A61M 25/04* (2006.01)
  *A61M 25/01* (2006.01)
  *A61M 25/00* (2006.01)
  *A61B 17/00* (2006.01)
  *A61B 90/30* (2016.01)
  *A61M 25/09* (2006.01)
  *A61B 34/20* (2016.01)
  *A61B 17/24* (2006.01)
  *A61M 25/10* (2013.01)

(52) U.S. Cl.
  CPC .......... *A61B 2034/2051* (2016.02); *A61B 2090/0807* (2016.02); *A61B 2090/0811* (2016.02); *A61B 2090/304* (2016.02); *A61B 2090/306* (2016.02); *A61B 2090/309* (2016.02); *A61B 2090/3937* (2016.02); *A61B 2217/007* (2013.01); *A61M 25/0041* (2013.01); *A61M 25/0102* (2013.01); *A61M 25/0113* (2013.01); *A61M 25/09041* (2013.01); *A61M 25/10* (2013.01); *A61M 2025/0008* (2013.01); *A61M 2025/09116* (2013.01); *A61M 2025/09175* (2013.01); *A61M 2029/025* (2013.01); *A61M 2205/583* (2013.01); *A61M 2205/587* (2013.01)

(56) References Cited

U.S. PATENT DOCUMENTS

| | | | |
|---|---|---|---|
| 7,654,997 | B2 | 2/2010 | Makower et al. |
| 7,720,521 | B2 | 5/2010 | Chang et al. |
| 7,803,150 | B2 | 9/2010 | Chang et al. |
| 8,123,722 | B2 | 2/2012 | Chang et al. |
| 8,190,389 | B2 | 5/2012 | Kim et al. |
| 8,320,711 | B2 | 11/2012 | Altmann et al. |
| 8,702,626 | B1 | 4/2014 | Kim et al. |
| 8,777,926 | B2 | 7/2014 | Chang et al. |
| 8,894,614 | B2 | 11/2014 | Muni et al. |
| 9,095,646 | B2 | 8/2015 | Chow et al. |
| 9,155,492 | B2 | 10/2015 | Jenkins et al. |
| 9,167,961 | B2 | 10/2015 | Makower et al. |
| 9,198,736 | B2 | 12/2015 | Kim et al. |
| 9,603,506 | B2 | 3/2017 | Goldfarb et al. |
| 9,931,026 | B2 | 4/2018 | Ha et al. |
| 9,962,530 | B2 | 5/2018 | Johnson et al. |
| 2003/0195526 | A1 | 10/2003 | Vilsmeier |
| 2006/0004323 | A1 | 1/2006 | Chang et al. |
| 2006/0069313 | A1 | 3/2006 | Couvillon, Jr. et al. |
| 2007/0208252 | A1 | 9/2007 | Makower |
| 2008/0009751 | A1* | 1/2008 | Berndt .............. A61B 1/07 600/478 |
| 2008/0183128 | A1 | 7/2008 | Morriss et al. |
| 2009/0287050 | A1* | 11/2009 | Barthel .............. A61M 29/02 600/115 |
| 2010/0022829 | A1* | 1/2010 | Irion .............. A61B 1/00124 600/109 |
| 2010/0030031 | A1 | 2/2010 | Goldfarb et al. |
| 2010/0249817 | A1* | 9/2010 | Mark .............. A61B 17/32002 606/170 |
| 2010/0292558 | A1* | 11/2010 | Saadat .............. A61B 1/00089 600/407 |
| 2010/0317956 | A1* | 12/2010 | Kartush .............. A61B 5/6859 600/380 |
| 2011/0004057 | A1 | 1/2011 | Goldfarb et al. |
| 2011/0060214 | A1 | 3/2011 | Makower |
| 2011/0125132 | A1* | 5/2011 | Krolik .............. A61M 25/10185 604/509 |
| 2012/0071856 | A1* | 3/2012 | Goldfarb .............. A61M 29/00 604/514 |
| 2012/0071857 | A1 | 3/2012 | Goldfarb et al. |
| 2012/0157968 | A1* | 6/2012 | Eldredge .............. A61M 15/08 604/514 |
| 2013/0013010 | A1 | 1/2013 | Rabineret et al. |
| 2013/0231736 | A1* | 9/2013 | Essinger .............. A61F 2/2436 623/2.11 |
| 2014/0018732 | A1* | 1/2014 | Bagaoisan .......... A61M 25/0136 604/95.04 |
| 2014/0200444 | A1 | 7/2014 | Kim et al. |
| 2014/0276328 | A1* | 9/2014 | Kesten .............. A61B 17/24 604/8 |
| 2014/0364725 | A1 | 12/2014 | Makower |
| 2016/0008083 | A1 | 1/2016 | Kesten et al. |
| 2016/0015944 | A1* | 1/2016 | Jenkins .............. A61M 25/09041 604/510 |
| 2016/0310042 | A1 | 10/2016 | Kesten et al. |
| 2016/0310714 | A1 | 10/2016 | Jenkins et al. |
| 2016/0367119 | A1* | 12/2016 | Ouyang .............. A61B 1/00052 |
| 2017/0042611 | A1* | 2/2017 | Parsonage .............. A61B 90/08 |
| 2017/0043142 | A1* | 2/2017 | Bareau .............. A61M 29/02 |
| 2017/0055818 | A1* | 3/2017 | Kermani .............. A61B 5/0084 |
| 2017/0056632 | A1* | 3/2017 | Jenkins .............. A61M 25/1011 |
| 2017/0120020 | A1* | 5/2017 | Lin .............. A61B 17/12104 |
| 2017/0224486 | A1* | 8/2017 | Delaloye .............. A61F 2/95 |
| 2018/0125567 | A1* | 5/2018 | Ciccone .............. A61B 1/00133 |
| 2018/0243046 | A1* | 8/2018 | Scott .............. A61B 90/39 |
| 2019/0209813 | A1* | 7/2019 | Stefanidis .......... A61M 25/0082 |

OTHER PUBLICATIONS

U.S. Appl. No. 62/555,719, entitled "Dilation System with Illuminating Orientation Indicator Features," filed Sep. 8, 2017.
U.S. Appl. No. 15/695,520, entitled "Sensor Guided Instrument with Penetrating Feature," filed Sep. 5, 2017.
International Search Report and Written Opinion dated Dec. 13, 2018 for Application No. PCT/IB2018/056769, 14 pgs.

* cited by examiner

DILATION SYSTEM WITH ILLUMINATING ORIENTATION INDICATOR FEATURES

This application claims the benefit of U.S. Provisional App. No. 62/555,719, entitled "Dilation System with Illuminating Orientation Indicator Features," filed Sep. 8, 2017, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Irvine, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein. An example of such an illuminating guidewire is the Relieva Luma Sentry™ Sinus Illumination System by Acclarent, Inc. of Irvine, Calif.

While several systems and methods have been made and used in ENT procedures, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIGS. 1A-1D show an exemplary dilation instrument assembly (10) that may be used to dilate the ostium of a paranasal sinus; to dilate some other passageway associated with drainage of a paranasal sinus; to dilate a Eustachian tube; or to dilate some other anatomical passageway (e.g., within the ear, nose, or throat, etc.). Dilation instrument assembly (10) of this example comprises a guidewire power source (12), an inflation source (14), an irrigation fluid source (16), and a dilation instrument (20).

In some versions, guidewire power source (12) comprises a source of light. In the present example, inflation source (14) comprises a source of saline. However, it should be understood that any other suitable source of fluid (liquid or otherwise) may be used. Also in the present example, irrigation fluid source (16) comprises a source of saline. Again, any other suitable source of fluid may be used. It should also be understood that irrigation fluid source (16) may be omitted in some versions.

Dilation instrument (20) of the present example comprises a handle body (22) with a guidewire slider (24), a guidewire spinner (26), and a dilation catheter slider (28) movably coupled to handle body (22). Handle body (22) is sized and configured to be gripped by a single hand of a human operator. Sliders (24, 28) and spinner (26) are positioned and configured to be manipulated by the same hand that grasps handle body (22). It should therefore be understood that dilation instrument (20) may be fully operated by a single hand of a human operator. As described in greater detail below, dilation instrument (20) further comprises a guidewire (30), a dilation catheter (40), and a guide catheter (60).

A. Exemplary Guide Catheter

Guide catheter (60) is removably received by and extends distally from a distal end of handle body (22). Guide catheter (60) includes a proximal hub (62) (see FIG. 3A) and a tubular shaft (64) extending distally from proximal hub (62). Catheter shaft (64) has a straight proximal catheter shaft portion (66), and a bent distal catheter shaft portion (68) terminating at an open distal end (70) defining an atraumatic tip. Distal catheter shaft portion (68) may have a smaller diameter than proximal catheter shaft portion (66). Proximal hub (62) is configured to releasably secure guide catheter (60) to handle body (22), and tubular shaft (64) is configured to slidably receive and guide a dilation catheter (40) therethrough. As described below, guide catheter (60) is selectively positionable in a plurality of rotational orientations relative to handle body (22) to facilitate access to various anatomical structures within a patient, such as ostia of various paranasal sinuses.

In the present example, distal catheter shaft portion (68) includes a preformed bend (72) that causes open distal end (70) to open along an axis that is angled relative to a longitudinal axis defined by proximal catheter shaft portion (66). Proximal and distal catheter shaft portions (66, 68) are each formed of a substantially rigid material (e.g., rigid metal, and/or rigid plastic, etc.), such that guide catheter (60) maintains a consistent configuration of bend (72) during use of dilation instrument (20). For instance, proximal catheter shaft portion (66) may be formed of a first rigid material, and distal catheter portion (68) may be formed of a second, less rigid material.

Figure 2:
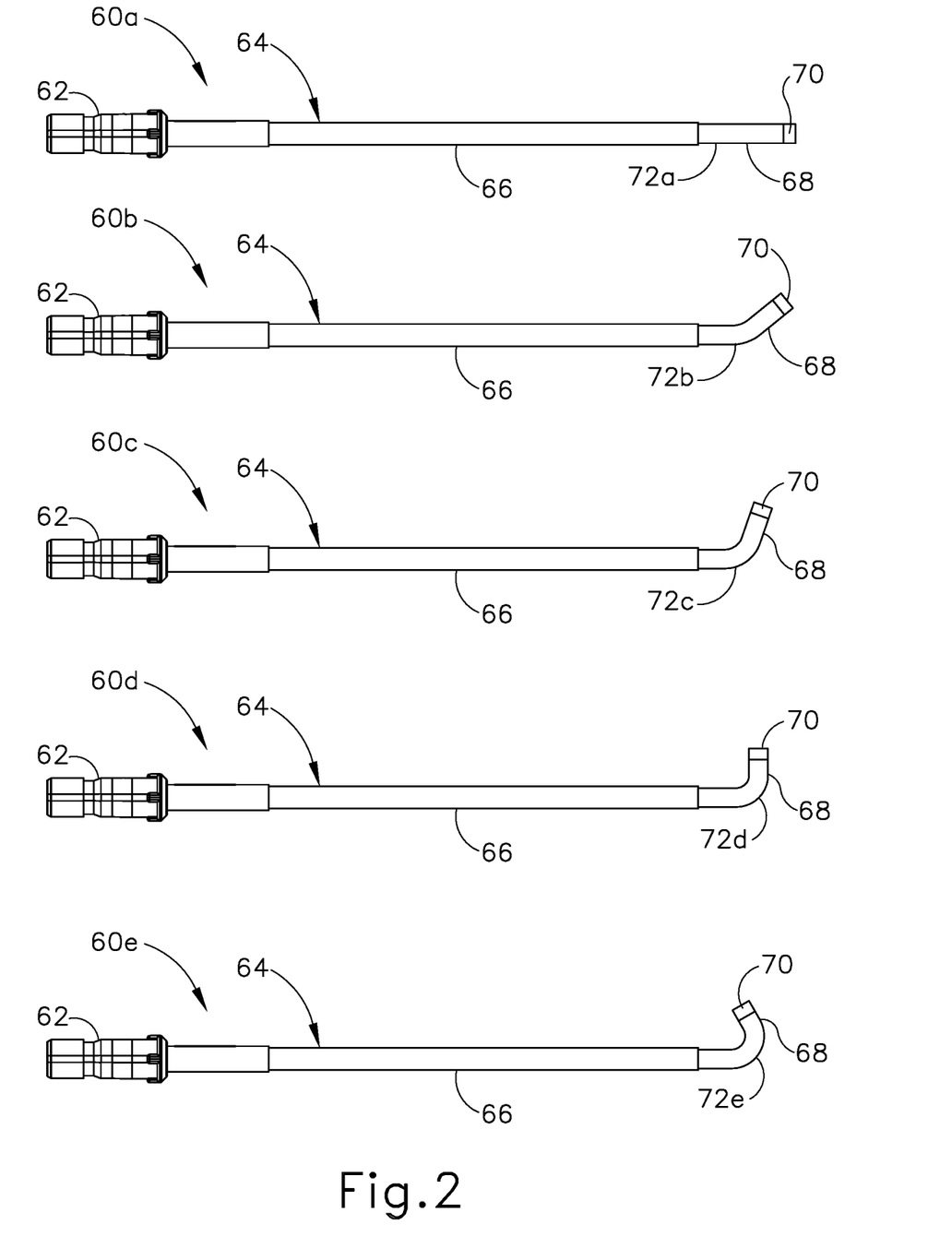
FIG. 2 depicts a plurality of exemplary variations of a guide catheter of the dilation instrument of FIG. 1A.

As shown in FIG. 2, bend (72) of distal catheter shaft portion (68) may be formed with a variety of suitable bend angles. Each different bend angle may facilitate access to a corresponding paranasal sinus or other anatomical structure(s). For instance, guide catheter (60a) has a preformed bend (72a) defining a bend angle of approximately 0 degrees. Guide catheter (60b) has a preformed bend (72b) defining a bend angle of approximately 30 degrees. Guide catheter (60c) has a preformed bend (72c) defining a bend angle of approximately 70 degrees. Guide catheter (60d) has a preformed bend (72d) defining a bend angle of approximately 90 degrees. Guide catheter (60e) has a preformed bend (72e) defining a bend angle of approximately 110 degrees. It will be understood that these bend angles are merely exemplary, and that guide catheter (60) may be provided with a bend angle of any suitable degree.

By way of example only, guide catheters (60, 60a, 60b, 60c, 60d, 60e) may be constructed and operable in accordance with at least some of the teachings of U.S. Pub. No. 2006/0004323, entitled "Apparatus and Methods for Dilating and Modifying Ostia of Paranasal Sinuses and Other Intranasal or Paranasal Structures," published Jan. 5, 2006, now abandoned, the disclosure of which is incorporated by reference herein; U.S. Pat. No. 8,894,614, entitled "Devices, Systems, and Methods Useable for Treating Frontal Sinusitis," issued Nov. 25, 2014, the disclosure of which is incorporated by reference herein; U.S. Pat. No. 7,654,997, entitled "Devices, Systems and Methods for Diagnosing and Treating Sinusitis and Other Disorders of the Ears, Nose and/or Throat," issued Feb. 2, 2010, the disclosure of which is incorporated by reference herein; and/or U.S. Pat. No. 7,803,150, entitled "Devices, Systems and Methods Useable for Treating Sinusitis," issued Sep. 28, 2010.

The disclosure of which is incorporated by reference herein.

B. Exemplary Guidewire

Figure 1A:
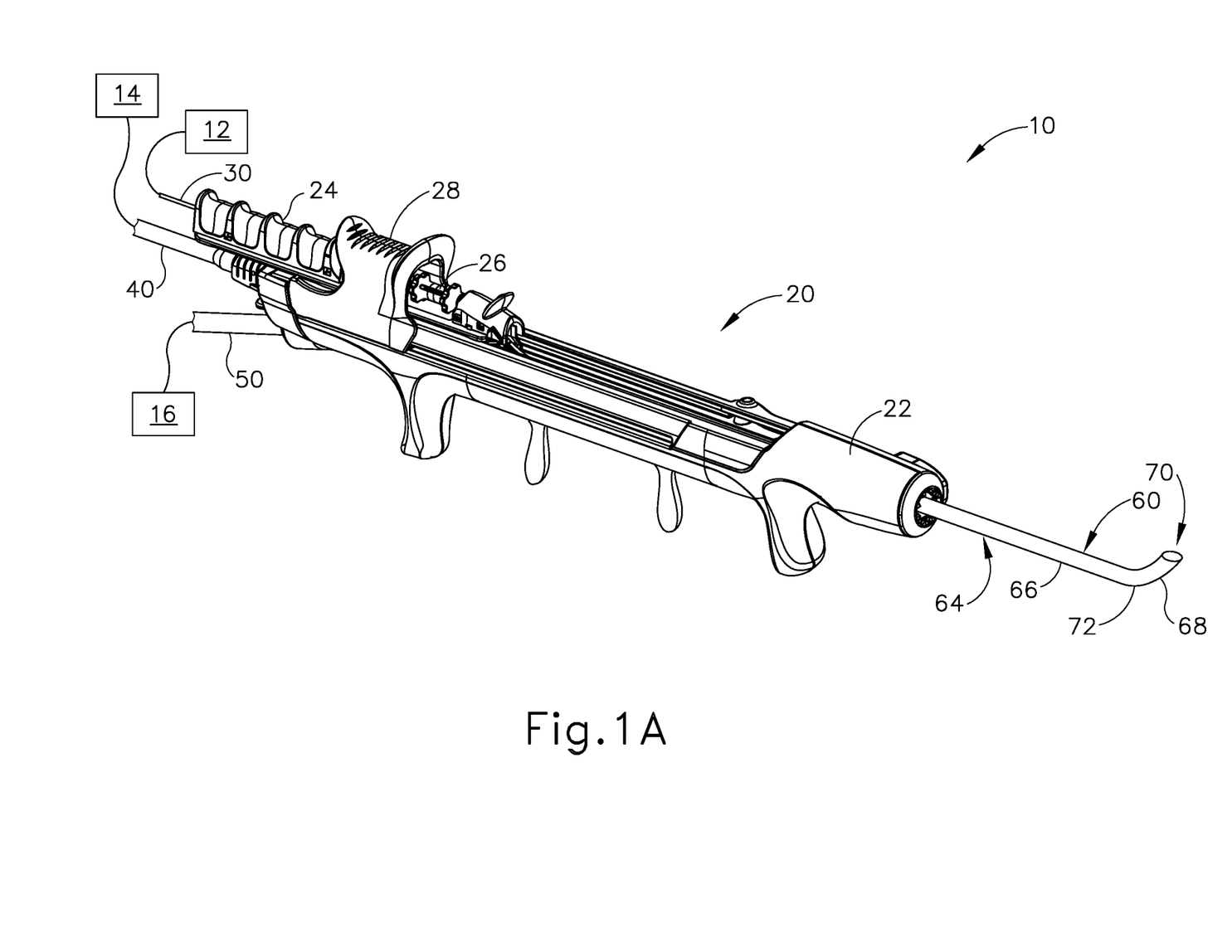
FIG. 1A depicts a perspective view of an exemplary dilation instrument assembly including a dilation instrument, showing a guidewire in a proximal position, and a dilation catheter in a proximal position.
Figure 1B:
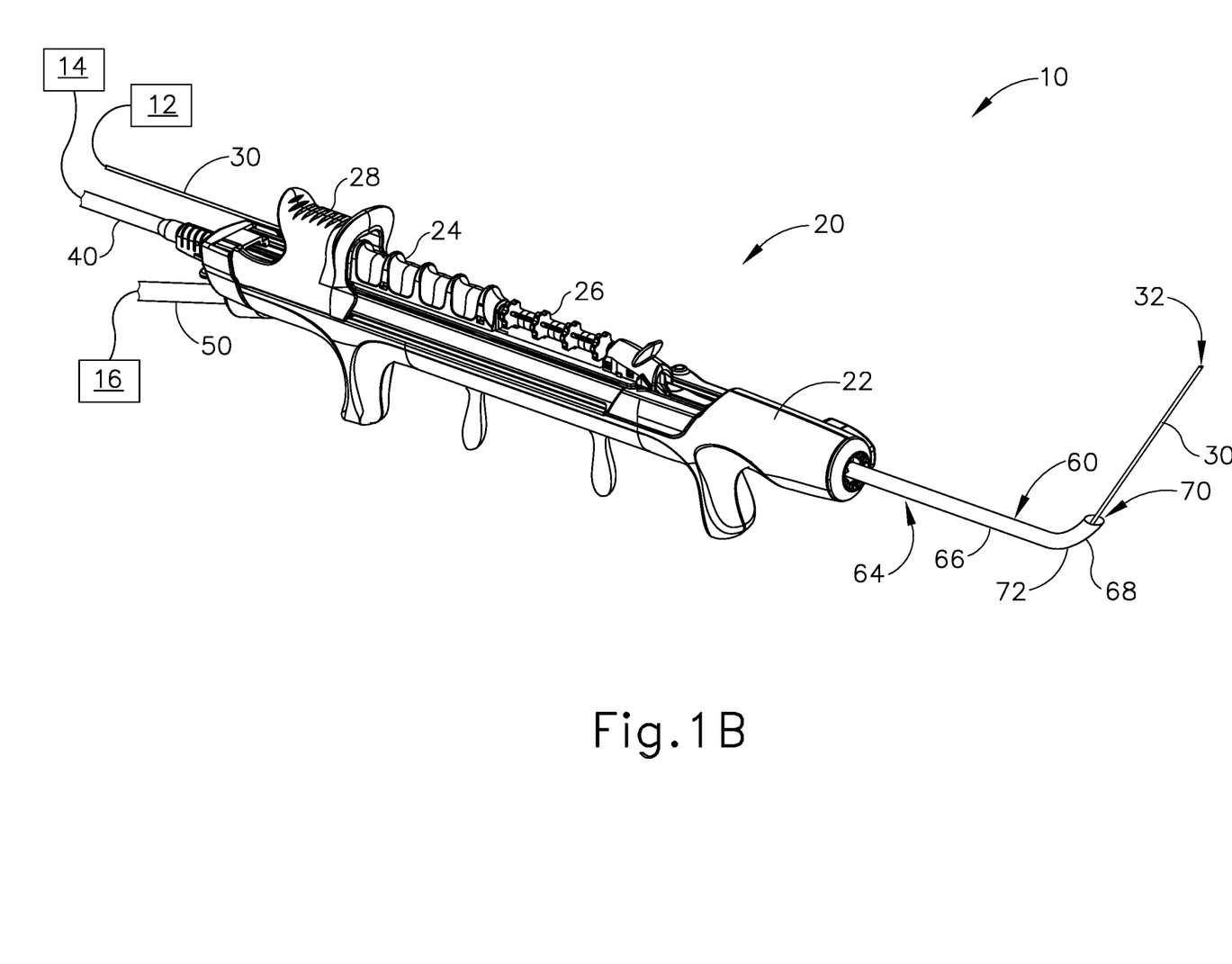
FIG. 1B depicts a perspective view of the dilation instrument assembly of FIG. 1A, showing the guidewire in a distal position, and the dilation catheter in the proximal position.

Guidewire (30) of dilation instrument (20) is slidably and coaxially disposed within guide catheter (60). Guidewire slider (24) is secured to guidewire (30) such that translation of guidewire slider (24) relative to handle body (22) provides corresponding translation of guidewire (30) relative to handle body (22), through guide catheter (60). In particular, translation of guidewire slider (24) from a proximal position (FIG. 1A) to a distal position (FIG. 1B) causes corresponding translation of guidewire (30) from a proximal position (FIG. 1A) to a distal position (FIG. 1B). When guidewire (30) is in a distal position, a distal end (32) of guidewire (30) protrudes distally from open distal end (70) of guide catheter (60). Guidewire spinner (26) is operable to rotate guidewire (30) about the longitudinal axis of guidewire (30). Guidewire spinner (26) is coupled with guidewire slider (24) such that guidewire spinner (26) translates longitudinally with guidewire slider (24).

In some versions, at least a portion of the length of guidewire (30) (e.g., approximately 7 inches) may be coated in one or more materials, such as silicone, for example. Various other suitable coating materials will be apparent to those of ordinary skill in the art in view of the teachings herein. Additionally, in some versions, a distal portion of guidewire (30) may include a preformed bend, for example as disclosed in U.S. Provisional Pat. App. No. 62/453,220, entitled "Navigation Guidewire with Interlocked Coils," filed Feb. 1, 2017, the disclosure of which is incorporated by reference herein. In such versions, the preformed bend and the rotatability provided via guidewire spinner (26) may facilitate alignment and insertion of distal end (32) into a sinus ostium, a Eustachian tube, or another passageway to be dilated.

Guidewire (30) may further include at least one optical fiber extending to a lens or other optically transmissive feature arranged at distal end (32). This optical fiber may be in optical communication with guidewire power source (12), such that light may be communicated from guidewire power source (12) to distal end (32). In such versions, guidewire (30) may provide transillumination through a patient's skin in order to provide visual feedback to the operator indicating that distal end (32) has reached a targeted anatomical structure. By way of example only, guidewire (30) may be configured in accordance with at least some of the teachings of U.S. Pat. No. 9,155,492, entitled "Sinus Illumination Lightwire Device," issued Oct. 13, 2015, the disclosure of which is incorporated by reference herein. In some versions, guidewire (30) may be configured similar to the Relieva Luma™ Sinus Illumination System by Acclarent, Inc. of Irvine, Calif.

In addition to or in lieu of including one or more optical fibers, guidewire (30) may include a sensor and at least one wire that enables guidewire (30) to provide compatibility with an image guided surgery (IGS) navigation system. In that regard, dilation instrument assembly (10) may be implemented as a component of an IGS navigation system, which may be constructed and operable in accordance with at least some of the teachings of U.S. patent application Ser. No. 15/695,520, entitled "Sensor Guided Instrument with Penetrating Feature," filed Sep. 5, 2017, issued as U.S. Pat No. 10,835,327 on Nov. 17, 2020, the disclosure of which is incorporated by reference herein; U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein; U.S. Pub. No. 2016/0310042, entitled "System and Method to Map Structures of Nasal Cavity," published Oct. 27, 2016, issued as U.S. Pat. No. 10,362,965 on Jul. 30, 2019, the disclosure of which is incorporated by reference herein; U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Such an IGS navigation system may be further constructed and operable in accordance with at least some of the teachings of U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pat. Pub. No. 2014/0200444, entitled "Guidewires for Performing Image Guided Procedures," published Jul. 17, 2014, now abandoned, the disclosure of which is incorporated by reference herein; U.S. Pat. No. 9,198,736, entitled "Adapter for Attaching Electromagnetic Image Guidance Components to a Medical Device," issued Dec. 1, 2015, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein; U.S. Pat. No. 9,167,961, entitled "Methods and Apparatus for Treating Disorders of the Ear Nose and Throat," issued Oct. 27, 2015, the disclosure of which is incorporated by reference herein; and U.S. Pat. Pub. No. 2007/0208252, entitled "Systems and Methods for Performing Image Guided Procedures within the Ear, Nose, Throat and Paranasal Sinuses," published Sep. 6, 2007, now abandoned, the disclosure of which is incorporated by reference herein.

Various other features and operabilities that may be incorporated into guidewire (30) will be apparent to those of ordinary skill in the art in view of the teachings herein.

C. Exemplary Dilation Catheter

Figure 1C:
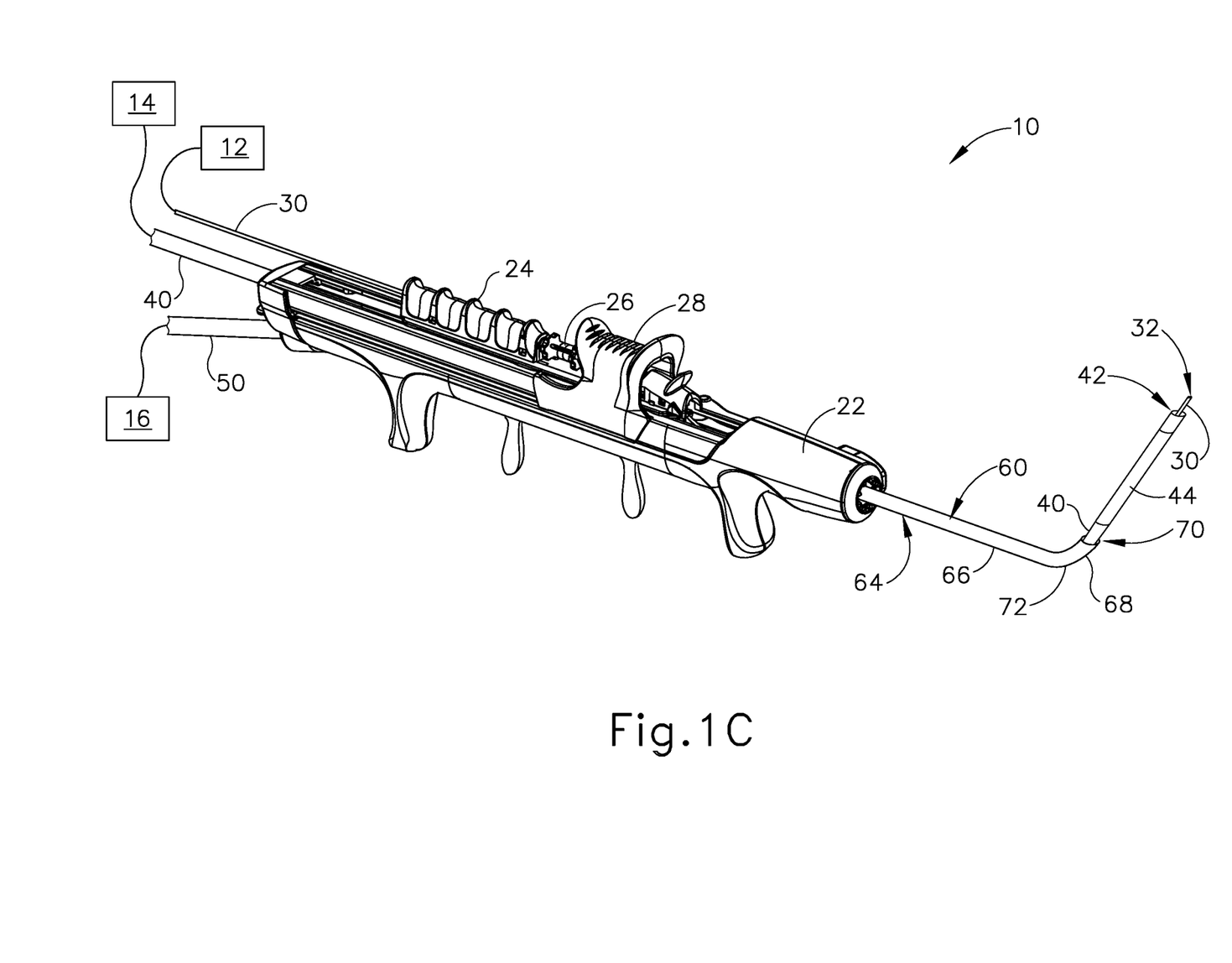
FIG. 1C depicts a perspective view of the dilation instrument assembly of FIG. 1A, showing the guidewire in a distal position, the dilation catheter in a distal position, and a dilator in a non-dilated state.

Dilation catheter (40) of dilation instrument (20) is slidably and coaxially disposed within guide catheter (60), and over guidewire (30). Dilation catheter slider (28) is secured to dilation catheter (40) such that translation of dilation catheter slider (28) relative to handle body (22) provides corresponding translation of dilation catheter (40) relative to handle body (22). In particular, translation of dilation catheter slider (28) from a proximal position (FIG. 1B) to a distal position (FIG. 1C) causes corresponding translation of dilation catheter (40) from a proximal position (FIG. 1B) to a distal position (FIG. 1C). When dilation catheter (40) is in a distal position, a distal portion of dilation catheter (40) protrudes distally from open distal end (70) of guide catheter (60). As can also be seen in FIG. 1C, a distal portion of guidewire (30) protrudes distally from an open distal end (42) of dilation catheter (40) when guidewire (30) and dilation catheter (40) are both in distal positions.

Figure 1D:
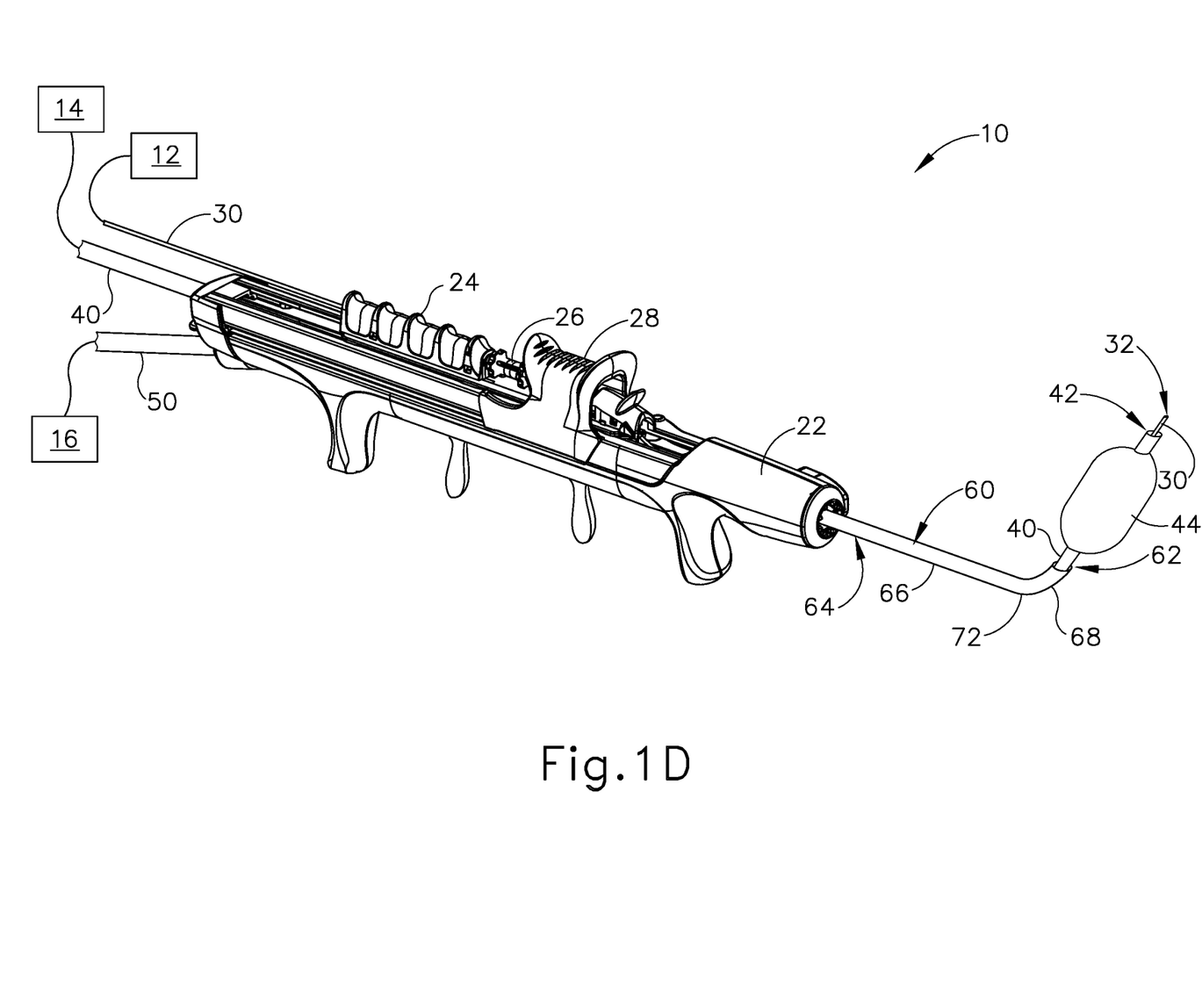
FIG. 1D depicts a perspective view of the dilation instrument assembly of FIG. 1A, showing the guidewire in a distal position, the dilation catheter in the distal position, and the dilator in a dilated state.

Dilation catheter (40) of the present example includes a dilation member in the form of a non-extensible balloon (44)

located just proximal to open distal end (42) of dilation catheter (40). Balloon (44) is in fluid communication with inflation source (14). Inflation source (14) is configured to communicate fluid (e.g., saline, etc.) to and from balloon (44) to thereby transition balloon (44) between a non-inflated state and an inflated state. FIG. 1C shows balloon (44) in a non-inflated state. FIG. 1D shows balloon (44) in an inflated state. In some versions, inflation source (14) comprises a manually actuated source of pressurized fluid. In some such versions, the manually actuated source of pressurized fluid is configured and operable in accordance with at least some of the teachings of U.S. Pat. No. 9,962,530, entitled "Inflator for Dilation of Anatomical Passageway," issued May 8, 2018, the disclosure of which is incorporated by reference herein. Other suitable configurations that may be used to provide a source of pressurized fluid will be apparent to those of ordinary skill in the art in view of the teachings herein.

Though not shown, it should be understood that dilation catheter (40) may include at least first and second, separate lumens that are in fluid isolation relative to each other. The first lumen may provide a pathway for fluid communication between balloon (44) and inflation source (14), while the second lumen provides a pathway to slidably receive guidewire (30).

While dilation catheter (40) of the present example is configured to transition between a non-dilated state (FIG. 1C) and a dilated state (FIG. 1D) based on the communication of fluid to and from balloon (44), it should be understood that dilation catheter (40) may include various other kinds of structures to serve as a dilator. By way of example only, balloon (44) may be replaced with a mechanical dilator in some other versions. Dilation catheter (40) may be constructed and operable in accordance with any of the various references cited herein. In some versions, dilator catheter (40) is configured and operable similar to the Relieva Ultirra™ Sinus Balloon Catheter by Acclarent, Inc. of Irvine, Calif. In some other versions, dilator catheter (40) is configured and operable similar to the Relieva Solo Pro™ Sinus Balloon Catheter by Acclarent, Inc. of Irvine, Calif. Other suitable variations of dilation catheter (40) will be apparent to those of ordinary skill in the art in view of the teachings herein.

In the present example, guidewire (30) is coaxially disposed within dilation catheter (40), which is coaxially disposed within guide catheter (60). In some other versions, guidewire (30) is omitted and dilation catheter (40) is slidably disposed about the exterior of an internal malleable guide member. In some other versions, guidewire (30) is slidably disposed about the exterior of the internal malleable guide member, and dilation catheter (40) is slidably disposed about the exterior of guidewire (30). In still other versions, guidewire (30) is slidably disposed within the interior of the malleable guide member, and dilation catheter (40) is slidably disposed about the exterior of the malleable guide member.

By way of example only, versions of dilation instrument (20) that include a malleable guide member may be constructed and operable in accordance with at least some of the teachings of U.S. Pub. No. 2016/0310714, entitled "Balloon Dilation System with Malleable Internal Guide," published Oct. 27, 2016, issued as U.S. Pat. No. 10,137,285 on Nov. 27, 2018, the disclosure of which is incorporated by reference herein. As another merely illustrative example, versions of dilation instrument (20) that include a malleable guide member may be constructed and operable in accordance with at least some of the teachings of U.S. Pub. No. 2017/0120020, entitled "Apparatus for Bending Malleable Guide of Surgical Instrument," published May 4, 2017, issued as U.S. Pat. No. 10,137,286 on Nov. 27, 2018, the disclosure of which is incorporated by reference herein; and/or U.S. Pub. No. 2012/0071857, entitled "Methods and Apparatus for Treating Disorders of the Sinuses," published Mar. 22, 2012, now abandoned, the disclosure of which is incorporated by reference herein.

D. Exemplary Irrigation Features

In some instances, it may be desirable to irrigate an anatomical site. For instance, it may be desirable to irrigate a paranasal sinus and nasal cavity after dilation catheter (40) has been used to dilate an ostium or other drainage passageway associated with the paranasal sinus. Such irrigation may be performed to flush out blood, etc. that may be present after the dilation procedure. In some such cases, guide catheter (60) may be allowed to remain in the patient while guidewire (30) and dilation catheter (40) are removed. A dedicated irrigation catheter (not shown) may then be inserted into guide catheter (60) and coupled with irrigation fluid source (16) via tube (50), to enable irrigation of the anatomical site in the patient. An example of an irrigation catheter that may be fed through guide catheter (60) to reach the irrigation site after removal of dilation catheter (60) is the Relieva Vortex® Sinus Irrigation Catheter by Acclarent, Inc. of Irvine, Calif. Another example of an irrigation catheter that may be fed through guide catheter (60) to reach the irrigation site after removal of dilation catheter (40) is the Relieva Ultirra® Sinus Irrigation Catheter by Acclarent, Inc. of Irvine, Calif.

In some other versions, dilation catheter (40) includes an additional irrigation lumen and an associated set of irrigation ports near distal end (42), such that dilation catheter (40) may be coupled with irrigation fluid source (16) via tube (50). Thus, a separate, dedicated irrigation catheter is not necessarily required in order to provide irrigation.

By way of example only, irrigation may be carried out in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, now abandoned, the disclosure of which is incorporated by reference herein; and U.S. Pat. No. 9,095,646, entitled "Devices and Methods for Transnasal Dilation and Irrigation of the Sinuses," issued Aug. 4, 2015. Of course, irrigation may be provided in the absence of a dilation procedure; and a dilation procedure may be completed without also including irrigation. It should therefore be understood that dilation fluid source (16) and tube (50) are merely optional.

In various other examples, dilation instrument assembly (10) may include additional or alternative features in accordance with at least some of the teachings of U.S. Pat. No. 8,777,926, entitled "Apparatus and Methods for Dilating and Modifying Ostia of Paranasal Sinuses and Other Intranasal or Paranasal Structures," issued Jul. 15, 2014, the disclosure of which is incorporated by reference herein.

II. Exemplary Features for Rotationally Orienting Guide Catheter Relative to Handle Body Various types of surgical procedures employing dilation instrument assembly (10) may be performed in a room or other location with relatively low (or "dim") light conditions. Such low light conditions enable a user to more easily locate and track distal end (32) of guidewire (30) equipped with a light emitting element that provides transillumination through the patient's skin, as described above. However, such low light ambient conditions may make it difficult for the user to efficiently operate other aspects of dilation instrument assembly (10). For example, the user may have difficulty seeing and properly coupling guide catheter (60) to handle body (22) during a procedure. The exemplary indicator features described below are configured to facilitate a user in properly identifying and positioning guide catheter (60) relative handle body (22) in a desired rotational orientation, particularly in low light conditions.

Figure 3A:
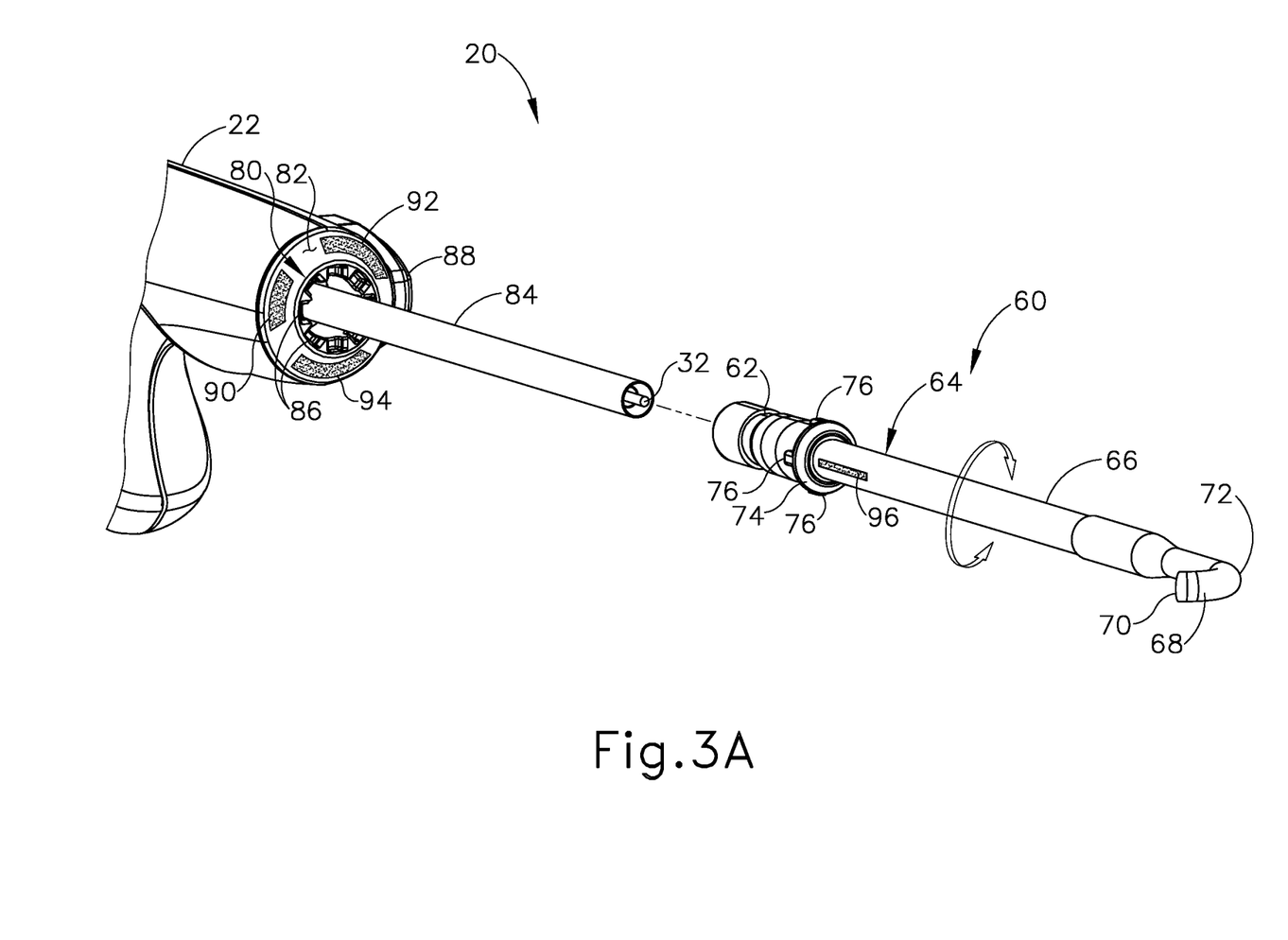
FIG. 3A depicts a perspective view of a distal portion of the dilation instrument of FIG. 1A in a partially disassembled state, showing additional details of the dilation instrument.
Figure 3B:
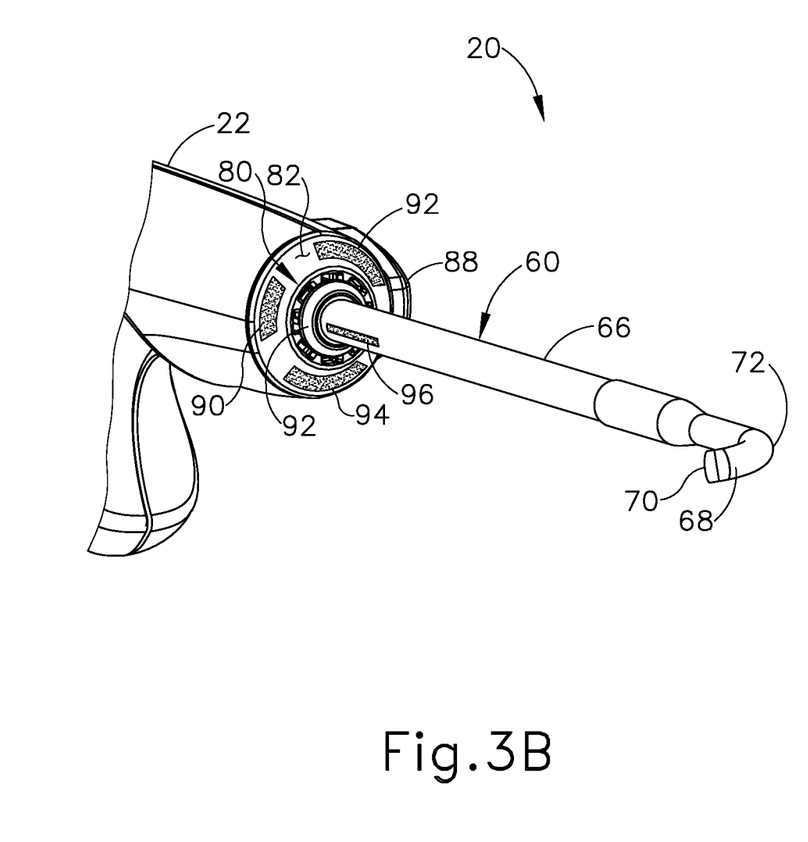
FIG. 3B depicts a perspective view of the distal portion of the dilation instrument of FIG. 3A in an assembled state.

FIGS. 3A and 3B show additional features of dilation instrument (20) that facilitate positioning of guide catheter (60) rotationally relative to handle body (22). As shown in FIG. 3A, handle body (22) includes a port (80) opening distally through a distally facing body surface (82). Port (80) is configured to receive and engage proximal hub (62) of guide catheter (60) to thereby couple guide catheter (60) to handle body (22). A tubular handle sheath (84) extends distally from port (80) and is configured to house guidewire (30) and dilation catheter (40) therein when in their proximal positions. Guide catheter (60) is configured to slide proximally over sheath (84) when being coupled to handle body (22).

Proximal hub (62) of guide catheter (60) includes an annular shoulder (74) arranged at a distal end of hub (62), and a plurality of axially extending ribs (76) arranged circumferentially about hub (62) at a proximal face of shoulder (74). Ribs (76) are configured to be received within and thereby lockingly engage circumferentially spaced recesses (86) formed in distally facing body surface (82) surrounding port (80). Shoulder (74) is configured to abut distally facing body surface (82) and thereby restrain guide catheter (60) proximally relative to handle body (22). In the present example, dilation instrument (10) includes four equally spaced ribs (76) and eight equally spaced recesses (86), which define eight possible rotational orientations in which guide catheter (60) may be secured relative to handle body (22). In other examples, various other quantities and arrangements of ribs (76) and recesses (86) may be provided. Each predefined rotational orientation of guide catheter (60) relative to handle body (22) is configured to position bent distal shaft portion (68) of guide catheter (60) at an optimal angle for accessing a particular anatomical structure, such as a particular paranasal sinus ostium or other drainage passageway within a head of a patient.

Proximal hub (62) of guide catheter (112) is secured axially within port (80) by a latch mechanism having an actuatable release button (88) arranged on an exterior side portion of handle body (22) for selectively releasing hub (62) from port (80). In other examples, hub (62) may be secured within port (80) by friction, detents, other types of latches such as a magnetic latch or an electromechanical latch, and/or by various other suitable features that will be readily apparent to those of ordinary skill in the art. In various examples, guide catheter (60) and handle body (22) may further configured in accordance with one or more teachings of U.S. Pat. Pub. No. 2017/0056632, entitled "Dilation Catheter with Expandable Stop Element," published Mar. 2, 2017, issued as U.S. Pat. No. 10,512,763 on Dec. 24, 2019, the disclosure of which is incorporated by reference herein.

As shown in FIG. 3A, handle body (22) includes a first indicator feature in the form of first, second, and third body indicator elements (90, 92, 94) spaced circumferentially about port (80) on distally facing body surface (82). Each body indicator element (90, 92, 94) extends circumferentially with a circumferential length that encompasses one or more recesses (86) and corresponding rotational orientations of guide catheter (60) relative to handle body (22). In the present example, first body indicator element (90) encompasses a first recess (86) that corresponds to a rotational orientation of guide catheter (60) suitable for accessing a frontal sinus of a patient. Second body indicator element (92) encompasses second and third recesses (86) that correspond to rotational orientations of guide catheter (60) suitable for accessing a right maxillary sinus of a patient. Third body indicator element (94) encompasses fourth and fifth recesses (86) that correspond to rotational orientations of guide catheter (60) suitable for accessing a left maxillary sinus of a patient.

Guide catheter (60) includes a second indicator feature in the form of an axially extending indicator element (96) arranged on a proximal end of proximal shaft portion (66). As shown in FIGS. 3A and 3B, during assembly of guide catheter (60) with handle body (22), guide catheter (60) may be rotated about its longitudinal axis to align catheter indicator element (96) with a selected one of body indicator elements (90, 92, 94). In this manner, the user may easily achieve a desired rotational orientation of guide catheter (60) relative to handle body (22) best suited for accessing a particular paranasal sinus ostium or other anatomical structure within the patient. Guide catheter (60) is selectively releasable from handle body (22), as described above, such that the rotational orientation of guide catheter (60) may be adjusted any number of times during a surgical procedure.

In some versions, indicator elements (90, 92, 94) are color coded, such that each indicator element (90, 92, 94) has a color differing from the colors of the other indicator elements (90, 92, 94). In such versions, the operator may be presented with a kit containing two or more modified versions of the guide catheters (60a, 60b, 60c, 60d, 60e) described above. Each modified guide catheter (60a, 60b, 60c, 60d, 60e) may include its own indicator element (96) with a unique color. In addition, or in the alternative, proximal hub (62) of each guide catheter (60a, 60b, 60c, 60d, 60e) may include its own color. In either case, the color of indicator element (96) and/or proximal hub (62) of each guide catheter (60a, 60b, 60c, 60d, 60e) may correspond with a particular color of an associated indicator element (90, 92, 94) of handle body (22). Since the angular position of each indicator element (90, 92, 94) may correspond with a desirable angular orientation for a particular guide catheter (60a, 60b, 60c, 60d, 60e) (i.e., to facilitate access to the particular anatomical structure associated with that particular guide catheter (60a, 60b, 60c, 60d, 60e)), the operator may visually observe the matching colors and position guide catheter (60a, 60b, 60c, 60d, 60e) accordingly when coupling a selected guide catheter (60a, 60b, 60c, 60d, 60e) with handle body (22).

By way of example only, guide catheter (60e) may be configured to provide access to a patient's maxillary sinus ostium; and indicator element (96) and/or proximal hub (62) of guide catheter (60e) may be colored blue. Indicator element (92) and/or indicator element (94) may be associated with angular positions that promote access to a patient's maxillary sinus, so indicator element (92) and/or indicator element (94) may be colored blue to visually indicate correspondence with guide catheter (60e) in particular.

In addition to indicating angular positions associated with particular kinds of guide catheters (60a, 60b, 60c, 60d, 60e), indicator elements (90, 92, 94) may also indicate which side of a patient's head is associated with a particular angular orientation. By way of example only, indicator element (92)

may include a letter "R" to indicate an angular position that facilitates access to a particular anatomical passageway (e.g., right maxillary sinus ostium) on the right side of a patient's head; while indicator element (94) may include a letter "L" to indicate an angular position that facilitates access to a particular anatomical passageway (e.g., left maxillary sinus ostium) on the left side of a patient's head.

A. Exemplary Phosphorescent Illuminating Indicator Elements

In the example shown in FIGS. 3A and 3B, each of indicator elements (90, 92, 94, 96) is formed of or otherwise includes a coating of a phosphorescent material configured to emit light (e.g., "glow") in low light conditions, such that each indicator element (90, 92, 94, 96) functions as an illuminating element. Exemplary phosphorescent materials may include strontium aluminate, for example. The phosphorescent characteristic of indicator elements (90, 92, 94, 96) enables a user to more easily identify indicator elements (90, 92, 94, 96) in low light conditions and position catheter indicator element (96) relative to a selected one of body indicator elements (90, 92, 94) to thereby achieve a desired rotational orientation of guide catheter (60) relative to handle body (22).

B. Exemplary Electrically-Powered Illuminating Indicator Elements

Figure 4:
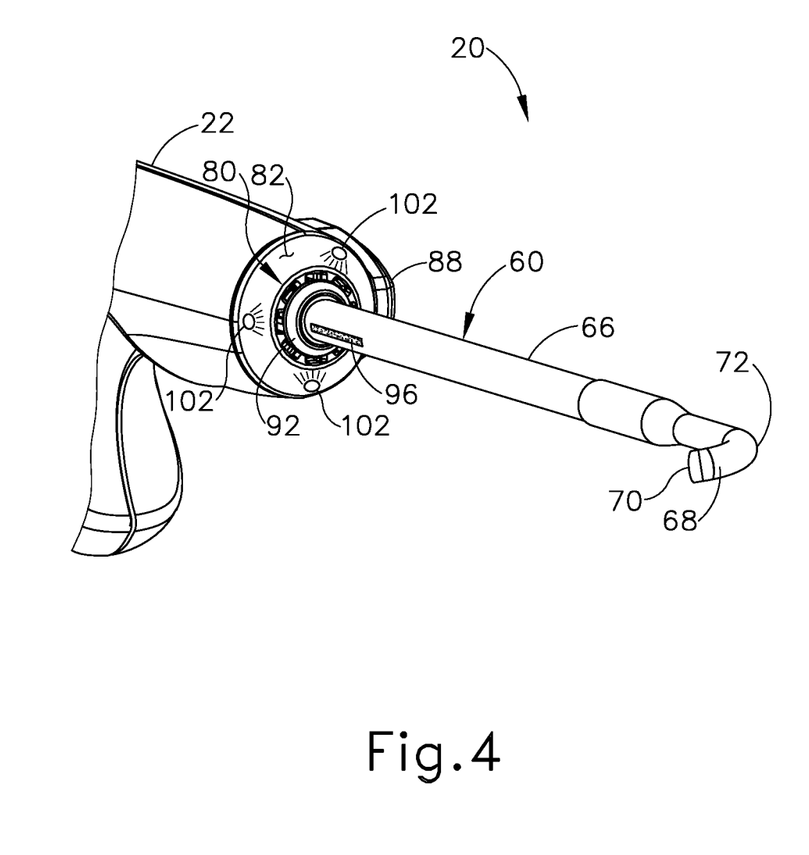
FIG. 4 depicts another exemplary dilation instrument.

FIG. 4 shows another exemplary dilation instrument (100) suitable for use with dilation instrument assembly (10). Dilation instrument (100) is similar to dilation instrument (20) described above, as indicated by use of like reference numerals, except as otherwise described below. In particular, handle body (22) includes a first illuminating indicator feature in the form of a plurality of electrically powered illuminating elements (102) (e.g., LEDs, etc.) arranged on handle body (22). In the present example, illuminating elements (102) are arranged circumferentially about port (80) on distally facing body surface (82) in place of body indicator elements (90, 92, 94). In other examples, illuminating elements (102) may be provided in combination with body indicator elements (90, 92, 94), with or without the phosphorescent material described above. In various such examples, each illuminating element (102) is positioned in alignment with a respective one or more recesses (86) corresponding to a respective one or more rotational orientations of guide catheter (60) relative to handle body (22).

Illuminating elements (102) may be electrically coupled with and powered by guidewire power source (12) (see FIGS. 1A-1D), or any other suitable power source arranged within or remotely from handle body (22). In some examples, illuminating elements (102) may be configured to emit light of a brightness sufficient to illuminate guide catheter indicator element (96), such that catheter indicator element (96) may be provided with or without phosphorescent material. In other examples, illuminating elements (102) may emit a lower brightness of light so as to "glow," in combination with catheter indicator element (96) being provided with a phosphorescent material. In still further examples, catheter indicator element (96) may be in the form of or otherwise include an electrically-powered illuminating element. As yet another merely illustrative example, illuminating elements (102) may emit light of different colors, to provide color-coded correspondence with particular kinds of guide catheters (60a, 60b, 60c, 60d, 60e) as described above.

Various other suitable quantities, arrangements, and combinations of illuminating elements (90, 92, 94, 96, 102) described above will be apparent to those of ordinary skill in the art in view the teachings provided herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a dilation catheter operatively coupled with the body, wherein the dilation catheter is configured to translate relative to the body between proximal and distal positions, wherein the dilation catheter includes a dilation member configured to dilate an anatomical passageway when the dilation catheter is in the distal position; (c) a guide catheter coupled to the body and defining a longitudinal axis, wherein the guide catheter is selectively positionable in a plurality of rotational orientations about the longitudinal axis relative to the body, wherein the guide catheter is configured to guide the dilation catheter therethrough between the proximal and distal positions; and (d) at least one illuminating indicator feature configured to emit light to facilitate positioning of the guide catheter in one or more of the rotational orientations.

Example 2

The apparatus of Example 1, wherein the at least one illuminating indicator feature is arranged on at least one of the body or the guide catheter.

Example 3

The apparatus of any one or more of the preceding Examples, wherein the at least one illuminating indicator feature includes at least one illuminating indicator element arranged on a distal portion of the body, wherein the at least one illuminating indicator element is configured to indicate the plurality of rotational orientations of the guide catheter relative to the body.

Example 4

The apparatus of Example 3, wherein the at least one illuminating indicator element comprises a plurality of illuminating indicator elements arranged on the distal portion of the body, wherein each of the illuminating indicator elements corresponds to a respective one of the rotational orientations of the guide catheter relative to the body.

Example 5

The apparatus of Example 4, wherein the at least one illuminating indicator feature further comprises an illuminating indicator element arranged on the shaft, wherein the illuminating indicator element on the shaft is configured to align with a corresponding one of the illuminating indicator elements on the body when the guide catheter is positioned in a respective one of the rotational orientations.

Example 6

The apparatus of any one or more of the preceding Examples, wherein the at least one illuminating indicator feature comprises a first illuminating indicator feature arranged on the body and a second illuminating indicator feature arranged on the guide catheter.

Example 7

The apparatus of Example 6, wherein the first illuminating indicator feature comprises a plurality of illuminating indicator elements arranged on a distal portion of the body.

Example 8

The apparatus of any one or more of Examples 6 through 7, wherein the guide catheter includes a shaft, wherein the second illuminating indicator feature is arranged on a proximal portion of the shaft.

Example 9

The apparatus of Example 8, wherein the shaft includes a bent distal portion, wherein the second illuminating indicator feature is arranged in alignment with the bent distal portion.

Example 10

The apparatus of any one or more of Examples 8 through 9, wherein the guide catheter further includes a proximal hub, wherein the shaft extends distally from the proximal hub, wherein the hub includes at least one rib configured to rotationally secure the proximal hub relative to the body in the plurality of rotational orientations.

Example 11

The apparatus of Example 10, wherein the body includes a distally facing port configured to receive the proximal hub, wherein the first illuminating indicator feature comprises a plurality of illuminating indicator elements arranged circumferentially about the port.

Example 12

The apparatus of any one or more of the preceding Examples, wherein the at least one illuminating indicator feature comprises a phosphorescent material.

Example 13

The apparatus of any one or more of the preceding Examples, wherein the at least one illuminating indicator feature includes an electrically powered illuminating indicator element.

Example 14

The apparatus of Example 13, wherein the electrically powered illuminating indicator element is arranged on a distally facing portion of the body.

Example 15

The apparatus of any one or more of Examples 13 through 14, wherein the electrically powered illuminating indicator element comprises a light emitting diode.

Example 16

An apparatus comprising: (a) a body; (b) a dilation catheter operatively coupled with the body, wherein the dilation catheter is configured to translate relative to the body between proximal and distal positions, wherein the dilation catheter includes a dilation member configured to dilate an anatomical passageway when the dilation catheter is in the distal position; (c) a guide catheter coupled to the body and defining a longitudinal axis, wherein the guide catheter is selectively positionable in at least first and second rotational orientations about the longitudinal axis relative to the body, wherein the guide catheter is configured to guide the dilation catheter therethrough between the proximal and distal positions; (d) first and second indicator elements arranged on the body; and (e) a third indicator element arranged on the guide catheter, wherein the guide catheter is positionable in the first rotational orientation relative to the body when the third indicator element is aligned with the first indicator element, wherein the guide catheter is positionable in the second rotational orientation relative to the body when the third indicator element is aligned with the second indicator element, wherein at least one of the first, second, or third indicator elements is configured to emit light to facilitate rotational positioning of the guide catheter relative to the body.

Example 17

The apparatus of Example 16, wherein the at least one of the first, second, or third indicator elements comprises a phosphorescent material.

Example 18

The apparatus of any one or more of Examples 16 through 17, wherein the first and second indicator elements are arranged on a distally facing portion of the body.

Example 19

An apparatus comprising: (a) a body; (b) a dilation catheter operatively coupled with the body, wherein the dilation catheter is configured to translate relative to the body between proximal and distal positions, wherein the dilation catheter includes a dilation member configured to dilate an anatomical passageway when the dilation catheter is in the distal position; (c) a guide catheter coupled to the body and defining a longitudinal axis, wherein the guide catheter is selectively positionable in a plurality of rotational orientations about the longitudinal axis relative to the body, wherein the guide catheter is configured to guide the dilation catheter therethrough between the proximal and distal positions; (d) a first indicator feature arranged on the body; and (e) a second indicator feature arranged on the guide catheter, wherein the second indicator feature is selectively positionable relative to the first indicator feature to thereby position the guide catheter in the plurality of rotational orientations, wherein at least one of the first or second indicator features comprises a phosphorescent material configured to emit light to facilitate rotational positioning of the guide catheter relative to the body.

Example 20

The apparatus of Example 19, wherein the first indicator feature comprises first and second indicator elements configured to emit light.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
(a) a body that includes a distal portion;
(b) a dilation catheter operatively coupled with the body, wherein the dilation catheter is configured to translate relative to the body between proximal and distal positions, wherein the dilation catheter includes a dilation member configured to dilate an anatomical passageway when the dilation catheter is in the distal position;
(c) a guide catheter coupled to the body and defining a longitudinal axis, wherein the guide catheter includes a proximal portion, wherein the guide catheter is selectively positionable in a plurality of rotational orientations about the longitudinal axis relative to the body, wherein the guide catheter is configured to guide the dilation catheter as the dilation catheter moves relative to the guide catheter between the proximal and distal positions;
(d) a first illuminating indicator feature arranged on the distal portion of the body, wherein the first illuminating indicator feature is configured to emit light to facilitate positioning of the guide catheter relative to the body in one or more of the rotational orientations; and
e) a second indicator feature arranged on the proximal portion of the guide catheter.

2. The apparatus of claim 1, wherein the first illuminating indicator feature includes at least one illuminating indicator element arranged on the distal portion of the body, wherein the at least one illuminating indicator element is configured to indicate the plurality of rotational orientations of the guide catheter relative to the body.

3. The apparatus of claim 2, wherein the at least one illuminating indicator element comprises a plurality of illuminating indicator elements arranged on the distal portion of the body, wherein each of the illuminating indicator elements corresponds to a respective one of the rotational orientations of the guide catheter relative to the body.

4. The apparatus of claim 3, wherein the guide catheter includes a shaft, wherein the second illuminating indicator feature includes an illuminating indicator element arranged on the shaft, wherein the illuminating indicator element on the shaft is configured to align with a corresponding one of the illuminating indicator elements on the body when the guide catheter is positioned in a respective one of the rotational orientations.

5. The apparatus of claim 1, wherein the first illuminating indicator feature comprises a plurality of illuminating indicator elements arranged on the distal portion of the body.

6. The apparatus of claim 1, wherein the guide catheter includes a shaft, wherein the second illuminating indicator feature is arranged on a proximal portion of the shaft.

7. The apparatus of claim 6, wherein the shaft includes a bent distal portion, wherein the second illuminating indicator feature is arranged in alignment with the bent distal portion.

8. The apparatus of claim 6, wherein the guide catheter further includes a proximal hub, wherein the shaft extends distally from the proximal hub, wherein the proximal hub includes at least one rib configured to rotationally secure the proximal hub relative to the body in the plurality of rotational orientations.

9. The apparatus of claim 8, wherein the body includes a distally facing port configured to receive the proximal hub, wherein the first illuminating indicator feature comprises a plurality of illuminating indicator elements arranged circumferentially about the port.

10. The apparatus of claim 1, wherein the first illuminating indicator feature comprises a phosphorescent material.

11. The apparatus of claim 1, wherein the first illuminating indicator feature includes an electrically powered illuminating indicator element.

12. The apparatus of claim 11, wherein the electrically powered illuminating indicator element is arranged on a distally facing portion of the body.

13. The apparatus of claim 11, wherein the electrically powered illuminating indicator element comprises a light emitting diode.

14. An apparatus comprising:
(a) a body that includes a distal portion;
(b) a dilation catheter operatively coupled with the body, wherein the dilation catheter is configured to translate relative to the body between proximal and distal positions, wherein the dilation catheter includes a dilation member configured to dilate an anatomical passageway when the dilation catheter is in the distal position;
(c) a guide catheter coupled to the body and defining a longitudinal axis, wherein the guide catheter is selectively positionable in at least first and second rotational orientations about the longitudinal axis relative to the body, wherein the guide catheter is configured to guide the dilation catheter as the dilation catheter moves relative to the guide catheter between the proximal and distal positions;
(d) first and second indicator elements arranged on a distal portion of the body; and
(e) a third indicator element arranged on the guide catheter,
wherein the guide catheter is positionable in the first rotational orientation relative to the body when the third indicator element is aligned with the first indicator element,
wherein the guide catheter is positionable in the second rotational orientation relative to the body when the third indicator element is aligned with the second indicator element,
wherein at least one of the first, second, or third indicator elements is configured to emit light to facilitate rotational positioning of the guide catheter relative to the body.

15. The apparatus of claim 14, wherein the at least one of the first, second, or third indicator elements comprises a phosphorescent material.

16. The apparatus of claim 14, wherein the first and second indicator elements are arranged on a distally facing portion of the body.

17. An apparatus comprising:
(a) a body;
(b) a dilation catheter operatively coupled with the body, wherein the dilation catheter is configured to translate relative to the body between proximal and distal positions, wherein the dilation catheter includes a dilation member configured to dilate an anatomical passageway when the dilation catheter is in the distal position;
(c) a guide catheter coupled to the body and defining a longitudinal axis, wherein the guide catheter includes a proximal portion, wherein the guide catheter is selectively positionable in a plurality of rotational orientations about the longitudinal axis relative to the body, wherein the guide catheter is configured to guide the dilation catheter as the dilation catheter moves relative to the guide catheter between the proximal and distal positions;
(d) a first indicator feature arranged on the body; and
(e) a second indicator feature arranged on the proximal portion of the guide catheter,
wherein the second indicator feature is selectively positionable relative to the first indicator feature to thereby position the guide catheter relative to the body in the plurality of rotational orientations,
wherein at least one of the first or second indicator features comprises a phosphorescent material configured to emit light to facilitate rotational positioning of the guide catheter relative to the body.

18. The apparatus of claim 17, wherein the first indicator feature comprises first and second indicator elements configured to emit light.

19. The apparatus of claim 17, wherein the body includes a distal portion, wherein the first indicator feature is arranged on the distal portion of the body.

* * * * *